US012229900B2

(12) United States Patent
Yanof et al.

(10) Patent No.: US 12,229,900 B2
(45) Date of Patent: Feb. 18, 2025

(54) AUGMENTED REALITY SYSTEM AND METHODS FOR STEREOSCOPIC PROJECTION AND CROSS-REFERENCING OF LIVE X-RAY FLUOROSCOPIC AND COMPUTED TOMOGRAPHIC C-ARM IMAGING DURING SURGERY

(71) Applicant: MEDIVIEW XR, INC., Cleveland, OH (US)

(72) Inventors: Jeffrey H. Yanof, Solon, OH (US); Peter Nicholas Braido, Linwood, MN (US)

(73) Assignee: MEDIVIEW XR, INC., Cleveland, OH (US)

( * ) Notice: Subject to any disclaimer, the term of this patent is extended or adjusted under 35 U.S.C. 154(b) by 386 days.

(21) Appl. No.: 17/885,912

(22) Filed: Aug. 11, 2022

(65) Prior Publication Data

US 2023/0050636 A1 Feb. 16, 2023

Related U.S. Application Data

(60) Provisional application No. 63/231,866, filed on Aug. 11, 2021.

(51) Int. Cl.
*G06T 19/00* (2011.01)
*G03H 1/04* (2006.01)
(Continued)

(52) U.S. Cl.
CPC ............. *G06T 19/006* (2013.01); *G03H 1/04* (2013.01); *G06T 5/50* (2013.01); *G06V 10/25* (2022.01);
(Continued)

(58) Field of Classification Search
CPC .............. G06T 19/006; G06T 5/50; G06T 2207/10021; G06T 2207/10081;
(Continued)

(56) References Cited

U.S. PATENT DOCUMENTS 10,895,906 B2 * 1/2021 West ..................... G06T 17/20
11,094,223 B2 * 8/2021 Lampotang ............ G09B 19/00
(Continued)

FOREIGN PATENT DOCUMENTS

| CN | 106909771 A | * | 6/2017 | ........... A61B 5/0013 |
| CN | 112584760 B | * | 8/2024 | ............. A61B 34/20 |
| WO | WO-2017145155 A1 | * | 8/2017 | ........... G02B 27/017 |

OTHER PUBLICATIONS

Written Opinion of the International Searching Authority dated Oct. 25, 2022.

*Primary Examiner* — Mahendra R Patel
(74) *Attorney, Agent, or Firm* — Jacob M. Ward; Ward Law Office LLC

(57) ABSTRACT

A method for performing a procedure on a patient includes acquiring a three-dimensional image of a location of interest on the patient and a two-dimensional image of the location of interest can be acquired. A computer system can relate the three-dimensional image with the two-dimensional image to form a holographic image dataset. The computer system can register the holographic image dataset with the patient. The augmented reality system can render a hologram based on the holographic image dataset from the patient. The hologram can include a projection of the three-dimensional image and a projection of the two-dimensional image. The practitioner can view the hologram with the augmented reality system and perform the procedure on the patient. The practitioner can employ the augmented reality system to visualize a point on the projection of the three-dimensional (Continued)

image and a corresponding point on the projection of the two-dimensional image during the procedure.

19 Claims, 5 Drawing Sheets

(51) Int. Cl.
*G06T 5/50* (2006.01)
*G06V 10/25* (2022.01)
*G06V 20/20* (2022.01)

(52) U.S. Cl.
CPC .... *G06V 20/20* (2022.01); *G06T 2207/10021* (2013.01); *G06T 2207/10081* (2013.01); *G06T 2207/10121* (2013.01); *G06T 2207/10132* (2013.01)

(58) Field of Classification Search
CPC .......... G06T 2207/10121; G06T 2207/10132; G03H 1/04; G06V 10/25; G06V 20/20; G02B 2027/014; A61B 90/36; A61B 2034/105; A61B 2034/2048; A61B 2034/2051; A61B 2034/2055; A61B 2090/363; A61B 2090/365; A61B 2090/376; A61B 2090/502
USPC .......................................................... 382/154
See application file for complete search history.

(56) References Cited

U.S. PATENT DOCUMENTS

| | | |
|---|---|---|
| 2013/0004052 A1 | 1/2013 | Chen et al. |
| 2016/0191887 A1 | 6/2016 | Casas |
| 2016/0220105 A1* | 8/2016 | Duret .................... H04N 23/56 |
| 2017/0172696 A1* | 6/2017 | Saget ...................... G06T 11/60 |
| 2018/0092698 A1* | 4/2018 | Chopra .................. A61B 90/39 |
| 2018/0200018 A1* | 7/2018 | Silva ....................... A61B 5/066 |
| 2019/0056693 A1* | 2/2019 | Gelman ................ G03H 1/0005 |
| 2019/0250558 A1* | 8/2019 | Javidi .................. G01N 21/453 |
| 2020/0375666 A1* | 12/2020 | Murphy ................. A61B 34/20 |
| 2021/0137634 A1* | 5/2021 | Lang ..................... A61B 34/20 |
| 2021/0161612 A1 | 6/2021 | Black et al. |
| 2021/0169587 A1 | 6/2021 | Martin, III et al. |
| 2021/0236209 A1 | 8/2021 | Black et al. |

\* cited by examiner

AUGMENTED REALITY SYSTEM AND METHODS FOR STEREOSCOPIC PROJECTION AND CROSS-REFERENCING OF LIVE X-RAY FLUOROSCOPIC AND COMPUTED TOMOGRAPHIC C-ARM IMAGING DURING SURGERY

CROSS REFERENCE TO RELATED APPLICATIONS

This application claims the benefit of U.S. Provisional Application Ser. No. 63/231,866, filed on Aug. 11, 2021. The entire disclosure of the above application is incorporated herein by reference.

FIELD

The present disclosure relates to an augmented reality system and, more specifically, to an augmented reality system for use during a surgical procedure.

INTRODUCTION

The statements in this section merely provide background information related to the present disclosure and may not constitute prior art.

Certain methods are used to register computed tomography (CT) imaging, including cone-beam computed tomography imaging (CBCT) and multidetector row computed tomography with C-arm system projections, but results are limited by display on a two-dimensional (2D) monitor. One common registration method is to reproject the CBCT data set at two projection angles (e.g., differing by 90 degrees) and compare the resulting image with the fluoroscopy image. A transformation is then determined to align the CBCT data with two fluoroscopic projections for subsequent visualization on the two-dimensional monitor.

Three-dimensional (3D) tomographic data can also be registered and fused on a 2D display with live fluoroscopy. The 3D registration is updated by tracking the motion of the C-arm in an integrated system. The limitation of this 2D fusion is that the 3D CT data can obscure the live fluoroscopic image. To prevent this, only lines delineating the target tissue or blood vessel are projected for the 3D data to the live fluoroscopy.

C-arm imaging data, including CBCT multiplanar reformation (MPR) and live fluoroscopy, is typically visualized during the procedure on one or more 2D display monitors either aside the patient table or in the imaging system control room. In other examples, a CBCT image volume can be re-projected in a perspective projection to form a simulated radiograph which can then be registered and fused with live fluoroscopy imaging. Further examples compare registration of live fluoroscopic images with 2D re-projected image volumes to register said image volume in C-arm coordinates.

There is a continuing need for a system, which uses perspective projection to augment a set of virtual objects derived from the imaging system so that they are congruent with the expected locations with respect to C-arm's geometry and physical pose, thus providing the 3D spatial relationship between the physical C-arm system and resulting x-ray C-arm system multimodality imaging results during the procedure.

SUMMARY

In concordance with the instant disclosure, a system, which uses perspective projection to augment a set of virtual objects derived from the imaging system so that they are congruent with the expected locations with respect to a C-arm's geometry and physical pose, thus providing the 3D spatial relationship between the physical C-arm system and resulting X-ray C-arm system multimodality imaging results during the procedure, has been surprisingly discovered.

In one embodiment, a method for performing a procedure on a patient utilizing an augmented reality system includes acquiring, by a first image acquisition system, an image dataset including multiple images. The image dataset can form a three-dimensional image of a location of interest on the patient. A two-dimensional image of the location of interest on the patient can be acquired. A computer system can relate the three-dimensional image with the two-dimensional image to form a holographic image dataset. The computer system can register the holographic image dataset with the patient. The augmented reality system can render a hologram based on the holographic image dataset from the patient for viewing by a practitioner. The hologram can include a projection of the three-dimensional image and a projection of the two-dimensional image. The practitioner can view the hologram with the augmented reality system and perform the procedure on the patient. The practitioner can employ the augmented reality system to visualize a point on the projection of the three-dimensional image and a corresponding point on the projection of the two-dimensional image during the procedure.

In another embodiment, a system for performing a procedure on a patient by a practitioner includes an augmented reality system configured to render a hologram. A first image acquisition system can be configured to acquire an image dataset from the patient. The image dataset can form a three-dimensional image of a location of interest on the patient. A computer system can have a processor and a memory. The computer system can be in communication with the augmented reality system and the first image acquisition system, and configured by machine-readable instructions to relate the three-dimensional image of the location of interest on the patient with a two-dimensional image of the location of interest on the patient to form a holographic image dataset; and register the holographic image dataset with the patient. The augmented reality system is configured to render the hologram based on the holographic image dataset from the patient for viewing by a practitioner, the hologram including a projection of the three-dimensional image and a projection the two-dimensional image and permit the practitioner to visualize a point on the projection of the three-dimensional image and a corresponding point on the projection of the two-dimensional image during the procedure.

The present technology projects, and cross-references, holographic (i.e., virtual) representations using the C-arm geometry and pose during imaging. A head-mounted stereoscopy display (HMD)—which updates and stabilizes the set of holographic projections (FIG. 1B) with head movement and viewing direction by tracking the location and orientation of the HMD—uses the C-arm system's geometry to project and cross-reference a set (or a subset) of holograms (e.g., based on live fluoroscopy, post-processed CBCT results, tracked instruments, and C-arm component models [e.g., x-ray tube and detector as well as imaging frustum and isocenter]). Fiducial markers on the patient's skin can also be imaged with CBCT to correct for gross patient motion relative to the imaging frustum.

The system of the present disclosure can accordingly be configured to improve the effectiveness, safety, and efficiency of 3D guidance and navigation on a C-arm (e.g., interventional radiology or angiography) system by registering, stereoscopically projecting (in the C-arm system's projection), and cross-referencing real-time (live) fluoroscopy projection imaging and cone-beam CT (CBCT) imaging results acquired during an interventional procedure. Live fluoroscopy imaging, which is a 2D perspective projection in the C-arm system's geometry, can be used to image dynamic motion such as interventional instruments, contrast enhancement, and organ motion with respiration. Whereas structures segmented from CBCT can provide 3D visualization of the anatomy in the interventional field. Stereoscopically projecting and cross-referencing CBCT and live fluoroscopy in the C-arm system's geometry (e.g., perspective projection, source-to-detector distance, patient table pose) can provide the synergistic advantages of 3D and live 2D imaging.

Holographically projecting the CBCT results and live fluoroscopic images in the head mounted display (HMD) 3D coordinate system and provides the means to cross-reference them leading to synergistic benefits from volume image data acquisition (with 4 second gantry rotation) and live fluoroscopy (multiple frames per second) on the systems patient table. Augmented Reality Head Mounted Displays (HMDs) enable stereoscopy holographic projection of 3D content relative to the physical C-arm which can enhance depth perception and spatial understanding.

The system and methods of the present disclosure can enable 3D stereoscopic projection, registration, and cross-referencing, in the C-arm system's geometry, of intraprocedural cone-beam CT imaging (CBCT) results, live fluoroscopy, and virtual (digitally modeled) C-arm components on a physical x-ray C-arm fluoroscopy system using an Augmented Reality (AR) Head Mounted Display (HMD). Three-dimensional CBCT and live two-dimensional fluoroscopy imaging can be stereoscopically projected as holograms in the HMD world coordinates in accordance with the C-arm projection geometry (including the C-arm isocenter, x-ray source-to-detector [SID] distance, field of view, and a tracked C-arm pose).

The AR system can track the pose of the C-arm associated with rotational CBCT and live fluoroscopic imaging in the 3D coordinate system of the HMD. Using the C-arm's projection geometry, the CBCT, live fluoroscopy (2D) holograms, as well as holographic representation of C-arm components, can be stereoscopically projected relative to the physical C-arm system, and spatially related to each other, in the HMD world coordinate system. Alternatively, an initial pose of the C-arm can be located in HMD world coordinates with an optical image target and tracked thereafter via integration with the C-arm and patient table motion control signals including information derived from the Digital Imaging and Communications of Medicine (DICOM) header file.

If the projective geometry of the C-arm fluoroscopy is not known to the AR system at the beginning of the procedure, spatial registration of the CBCT into the world coordinate system of the stereoscopic HMD can be performed using x-ray imageable combination markers (optical image target and x-ray fiducial markers) to localize the holographic CBCT data relative to x-ray fiducial markers located on the skin surface. Also, as an alternate to using the C-arm system's geometry, the holographic projection of the live fluoroscopic image can be manually positioned relative to the pose of the physical flat panel display.

A point located on the MPR or surface representation of the CBCT hologram, that can be interactively selected by the operator, can have a corresponding (e.g., cross referenced) location on the live fluoroscopic image. A holographic line segment can be projected between said corresponding points localized on the 3D CBCT hologram and a point localized on live fluoroscopic holographic projection display.

If a tracked surgical instrument is integrated and calibrated with the C-arm systems using said combination markers, a physical point located on the physical patient can have corresponding points located and cross-referenced, using a holographic line segment, on the CBCT and fluoroscopy-based holograms.

The C-arm projective frustum, based on the C-arm system's geometric model relating the fluoroscopic and CBCT data, can also be projected as holographic line segments in the world coordinates of the head mounted display for delineating the spatial relationship of the CBCT and live fluoroscopy holograms.

The pose of the C-arm's imaging and component holographic representation can be initially aligned with the physical C-arm. Alternatively, to enhance visualization of the set of holographic projection and eye-hand-coordination, the operator can interact with the holograms (e.g., using far or near interaction of the Mixed Reality Toolkit) to adjust the pose of the C-arm system's holographic representation including the imaging frustum and modeled (virtual) components based on the C-arm geometry, such as rotation about the C-arm's systems isocenter, relative to and cross-reference with the CBCT's holographic representation of the patient anatomy in order the plan an updated pose of the physical C-arm with less ionizing radiation burden and skin dose.

The reconstructed CBCT data can be holographically projected in HMD world coordinates as a combination of MPR and segmented surfaces. Segmentation of structures from CBCT images can be quickly performed intraprocedurally with a numerical CT threshold to segment bone and contrast enhance structures. Resulting segmented structures can be transmitted to the HMD in Object file format. The MPR images can be projected in orientations corresponding to the physical anatomical planes (axial, sagittal, and coronal). These three planes are mutually perpendicular MPR holograms that intersect at a point, where the latter can be interactively adjusted by the operator to update the images, and the intersection point can be projected and crossed referenced to holographic projection the live fluoroscopy stream.

A computed tomographic data set, acquired as a set of images, can be intraprocedurally transmitted to the HMD (and/or AR server) after reconstruction by the C-arm system from a set of X-ray projections acquired during x-ray tube rotation. The live fluoroscopic image stream can also be sent wirelessly to the HMD (via AR server) without appreciable temporal latency. The C-arm projection model associated with the CBCT and live fluoroscopic images can also be transmitted to the AR server prior to CBCT reconstruction or read from the CBCT image header.

A method of tracking interventional instruments, including needles and imaging probes (e.g., sonography [ultrasound] probe), can be used to register a virtual representation of the device in HMD world coordinates in co-registration with the set C-arm based holograms. The tracking method can be based on optical camera or electromagnetic measurements. The tracked device spatial registration can be based on a Combination (combo) markers that localize corresponding physical points in HMD world coordinate camera and the tracking measurement modality. As with the C-arm components, a holographic representation of the tracked instrument can be projected in co-registration with the CBCT and cross-reference to the live fluoroscopy imaging. Registration of the tracked CT and device holograms enable the intermitted use of fluoroscopy to facilitate the management of x-ray radiation dose burden.

Projection and cross-referencing of live fluoroscopic projection and CBCT holograms, in the C-arm system's geometry and pose, can be used to match the respiratory phase of physical patient ventilation or respiration to the phase that occurred during the acquisition of the CBCT. This will increase the tissue targeting accuracy associated with the CBCT-based holograms.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
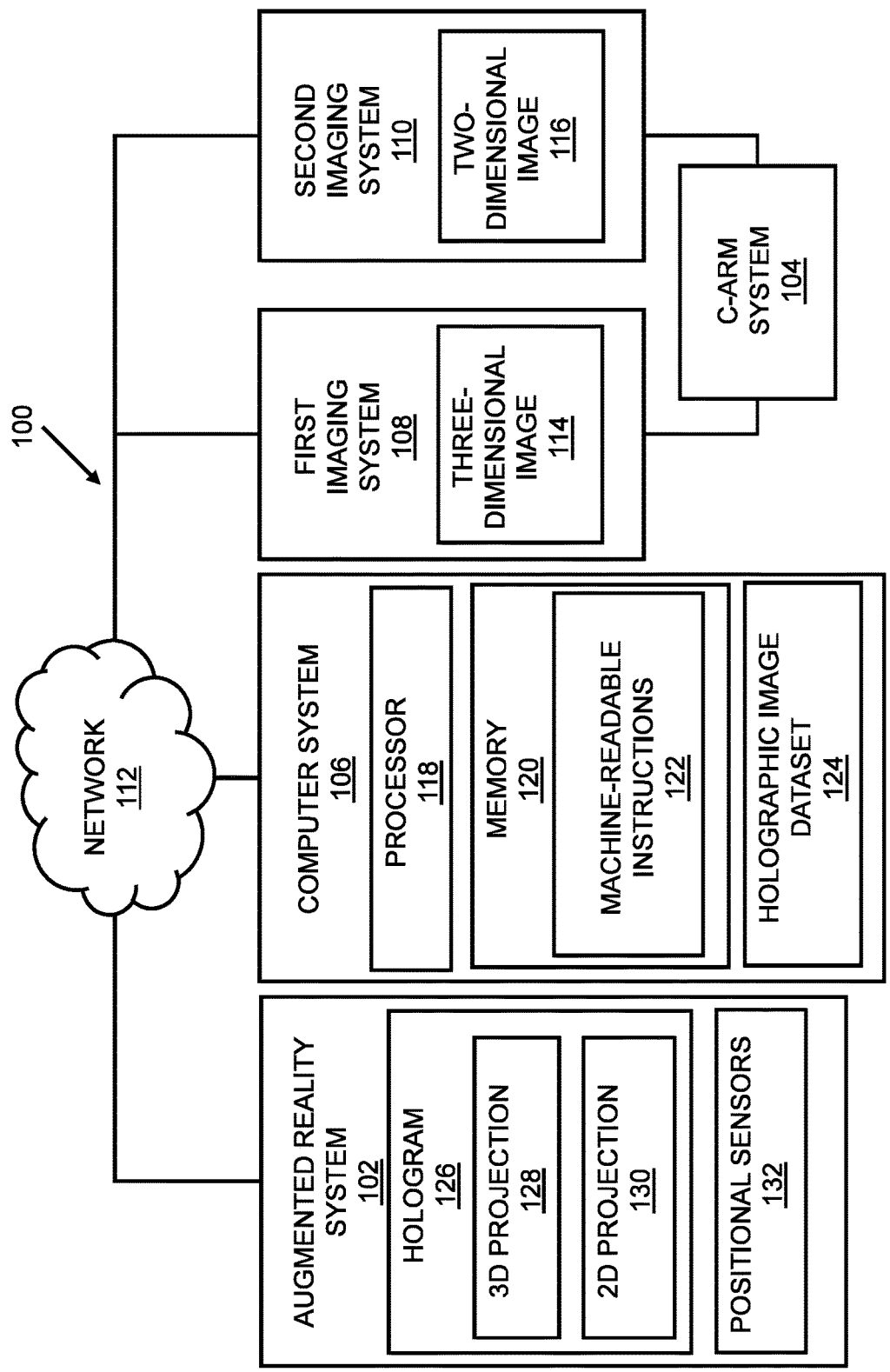
FIG. 1 is a schematic depicting a system for performing a procedure on a patient utilizing an augmented reality system.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

As used herein, the term "head-mounted device" or "headset" or "HMD" refers to a display device, configured to be worn on the head, that has one or more display optics (including lenses) in front of one or more eyes. These terms may be referred to even more generally by the term "augmented reality system," although it should be appreciated that the term "augmented reality system" is not limited to display devices configured to be worn on the head. In some instances, the head-mounted device can also include a non-transitory memory and a processing unit. An example of a suitable head-mounted device is a Microsoft HoloLens®.

As used herein, the terms "imaging system," "image acquisition apparatus," "image acquisition system" or the like refer to technology that creates a visual representation of the interior of a patient's body. For example, the imaging system can be a computed tomography (CT) system, a fluoroscopy system, a magnetic resonance imaging (MM) system, an ultrasound (US) system, or the like.

As used herein, the terms "coordinate system" or "augmented realty system coordinate system" refer to a 3D Cartesian coordinate system that uses one or more numbers to determine the position of points or other geometric elements unique to the particular augmented reality system or image acquisition system to which it pertains. For example, the headset coordinate system can be rotated, scaled, or the like, from a standard 3D Cartesian coordinate system.

As used herein, the terms "image data" or "image dataset" or "imaging data" refers to information recorded in 3D by the imaging system related to an observation of the interior of the patient's body. For example, the "image data" or "image dataset" can include processed two-dimensional or three-dimensional images or models such as tomographic images, e.g., represented by data formatted according to the Digital Imaging and Communications in Medicine (DICOM) standard or other relevant imaging standards.

As used herein, the terms "imaging coordinate system" or "image acquisition system coordinate system" refers to a 3D Cartesian coordinate system that uses one or more numbers to determine the position of points or other geometric elements unique to the particular imaging system. For example, the imaging coordinate system can be rotated, scaled, or the like, from a standard 3D Cartesian coordinate system.

As used herein, the terms "hologram", "holographic," "holographic projection", or "holographic representation" refer to a computer-generated image projected to a lens of a headset. Generally, a hologram can be generated synthetically (in an augmented reality (AR)) and is not related to physical reality.

As used herein, the term "physical" refers to something real. Something that is physical is not holographic (or not computer-generated).

As used herein, the term "two-dimensional" or "2D" refers to something represented in two physical dimensions.

As used herein, the term "three-dimensional" or "3D" refers to something represented in three physical dimensions. An element that is "4D" (e.g., 3D plus a time and/or motion dimension) would be encompassed by the definition of three-dimensional or 3D.

As used herein, the term "integrated" can refer to two things being linked or coordinated. For example, a coil-sensor can be integrated with an interventional device.

As used herein, the term "degrees-of-freedom" or "DOF" refers to a number of independently variable factors. For example, a tracking system can have six degrees-of-freedom (or 6DOF), a 3D point and 3 dimensions of rotation.

As used herein, the term "real-time" refers to the actual time during which a process or event occurs. In other words, a real-time event is done live (within milliseconds so that results are available immediately as feedback). For example, a real-time event can be represented within 100 milliseconds of the event occurring.

As used herein, the terms "subject" and "patient" can be used interchangeably and refer to any vertebrate organism.

As used herein, the term "registration" refers to steps of transforming tracking data and body image data to a common coordinate system and creating a holographic display of images and information relative to a body of a physical patient during a procedure, for example, as further described in U.S. Pat. No. 10,895,906 to West et al., and also applicant's co-owned U.S. patent application Ser. No. 17/110,991 to Black et al. and U.S. patent application Ser. No. 17/117,841 to Martin III et al., the entire disclosures of which are hereby incorporated herein by reference.

As used herein, the terms "interventional device" or "tracked instrument" refers to a medical instrument used during the medical procedure.

As used herein, the term "C-arm system" refers to a C-Arm—Fluoroscopy Machines having a C-arm and an imaging frustrum. An example C-arm system is the OEC Elite CFD, which is commercially available from General Electric (Boston, MA).

The present technology relates to ways of performing a procedure on a patient utilizing an augmented reality system. An embodiment of a holographic augmented reality system 100 for performing a procedure on a patient by a practitioner is shown in FIG. 1. The system 100 can be configured to use one or more perspective projections to augment a set of virtual objects derived from imaging systems to allow the practitioner to project and cross-reference images from multiple imaging systems. Advantageously, the system 100 of the present disclosure can accordingly improve the effectiveness, safety, and efficiency of three-dimensional guidance and navigation during a procedure by registering, stereoscopically projecting, and cross-referencing real-time fluoroscopy projection imaging and cone-beam computer topography (CBCT) imaging results acquired during the interventional procedure.

It should be appreciated that the system 100 of the present disclosure can be utilized in a variety of different procedures. As non-limiting examples, the procedures can include neurological procedures, cardiac procedures, oncology procedures, orthopedic procedures, gastroenterology procedures, orthodontic procedures, and dental procedures. A skilled artisan can employ the system 100 of the present disclosure, as desired, into any applicable procedure, as described herein.

With continued reference to FIG. 1, the system 100 can include an augmented reality system 102, a C-arm system 104, a computer system 106, and a first image acquisition system 108. In certain examples, the holographic augmented reality visualization and guidance system 100 can further include a second image acquisition system 110. It should be appreciated that the first image acquisition system 108 and the second image acquisition system 100 can be integrated within the C-arm system 104.

Each of the augmented reality system 102, the C-arm system 104, the first image acquisition system 108, and the second image acquisition system 110 may be selectively or permanently in communication with the computer system 106, for example, via a computer network 112. Other suitable instruments, tools, equipment, sub-systems, and the like for use with the holographic augmented reality visualization and guidance system 100, as well as other network means including wired and wireless means of communication between the components of the holographic augmented reality visualization and guidance system 100, may also be employed by the skilled artisan, as desired.

The first image acquisition system 108 is configured to acquire an image dataset of an area of interest from the patient. In particular, the first image acquisition system 108 can be configured to acquire the image dataset from the patient in a preoperative manner, in certain embodiments. The first image acquisition system 108 can be one of a cone-beam computed tomography imaging system (CBCT) or multidetector row computed tomography (CT) system. The first image acquisition system 108 can also include a weight bearing CT system or a dental CBCT system. The image dataset can be used to form a three-dimensional image 114 of the location of interest in the patient. The three-dimensional image can include multiplanar reformation of cone-beam computed tomography. Other suitable types of instrumentation for the first image acquisition system 108 may also be employed, as desired.

Likewise, the second image acquisition system 110 can be configured to acquire a two-dimensional image 116 from the location of interest on the patient. In particular, the second image acquisition system 110 can be configured to acquire the two-dimensional image from the patient in an intraoperative manner, and most particularly in real-time as the procedure is being undertaken. The second image acquisition system 100 can include various fluoroscopic devices. A skilled artisan can select a suitable second image acquisition system 100, as desired.

Although use of both the first image acquisition system 108 and the second image acquisition system 110 is shown and described herein, embodiments in which only one or the other of the first image acquisition system 108 and the second image acquisition system 110 is employed or embodiments where the two-dimensional image is one of the images of the image dataset 114, are considered to be within the scope of the present disclosure.

With continued reference to FIG. 1, the computer system 106 of the present disclosure has at least one processor 118 and at least one memory 120 on which tangible, non-transitory, machine-readable instructions 122 are stored.

The one or more processors 118 can perform functions associated with the operation of the holographic augmented reality visualization and guidance system 100. The one or more processors 118 can be any type of general or specific purpose processor. In some cases, multiple processors 118 can be utilized according to other embodiments. In fact, the one or more processors 118 can include one or more of general-purpose computers, special purpose computers, microprocessors, digital signal processors (DSPs), field-programmable gate arrays (FPGAs), application-specific integrated circuits (ASICs), and processors based on a multi-core processor architecture, as non-limiting examples.

The memory 120 can be one or more memories and of any type suitable to the local application environment, and can be implemented using any suitable volatile or nonvolatile data storage technology such as a semiconductor-based memory device, a magnetic memory device and system, an optical memory device and system, fixed memory, and removable memory. For example, the memory 120 can include of any combination of random access memory (RAM), read only memory (ROM), static storage such as a magnetic or optical disk, hard disk drive (HDD), or any other type of non-transitory machine or computer readable media. The instructions stored in the memory 120 can include program instructions or computer program code that, when executed by one or more processors 118, enable the holographic augmented reality visualization and guidance system 100 to perform tasks as described herein.

The machine-readable instructions 122 can include modules. The modules can be implemented as one or more of functional logic, hardware logic, electronic circuitry, software modules, and the like. The modules can include one or more of an augmented reality system module, an image acquiring module, an instrument tracking module, an image dataset registering module, a hologram rendering module, an image registering module, a trajectory hologram rendering module, and/or other suitable modules, as desired.

The computer system 106 is in communication with the augmented reality system 102, the C-arm system 104, and the first image acquisition system 108, and the second image acquisition system 110, for example, via the network 112, and is configured by the machine-readable instructions 122 to operate in accordance with the method 200 as described further herein. The computer system 106 can be separately provided and spaced apart from the augmented reality system 102 or can be provided together with the augmented reality system 102 as a singular one-piece unit, as desired.

It should be appreciated that the network 112 of the holographic augmented reality visualization and guidance system 100 can include a radio access network, such as LTE or 5G, a local area network (LAN), a wide area network (WAN) such as the Internet, or wireless LAN (WLAN), as non-limiting examples. It will be appreciated that this is not intended to be limiting, and that the scope of this disclosure includes implementations in which one or more computing platforms of the holographic augmented reality visualization and guidance system 100 can be operatively linked via some other communication coupling. The one or more one or more computing platforms can be configured to communicate with the networked environment via wireless or wired connections. In addition, in an embodiment, the one or more computing platforms can be configured to communicate directly with each other via wireless or wired connections. Examples of one or more computing platforms can include, but is not limited to, smartphones, wearable devices, tablets, laptop computers, desktop computers, Internet of Things (IoT) device, or other mobile or stationary devices such as standalone servers, networked servers, or an array of servers.

The computer system 106 can be configured to relate the three-dimensional image 114 of the image dataset with the two-dimensional image 116 to form a three-dimensional holographic image dataset 124. The computer system 106 can further be configured to register the holographic image dataset 124 with the patient and within the geometry of the C-arm system, as discussed in greater detail herein. The computer system 106 can relate the three-dimensional image 114 of the image dataset with the two-dimensional image 116 in accordance with the geometry of the C-arm (e.g., perspective projection, source-to-detector distance, patient table pose). Advantageously, the computer system 106 can allow for stereoscopic projection and cross-referencing of CBCT and live fluoroscopy in the C-arm system's geometry (e.g., perspective projection, source-to-detector distance, patient table pose), which can provide the synergistic advantages of three-dimensional and live two-dimensional imaging.

With continued reference to FIG. 1, the augmented reality system 102 is configured to render a hologram 126 based on the holographic image dataset from the patient for viewing by a practitioner. The hologram 126 can include a projection of the three-dimensional image 128 and a projection of the two-dimensional image 130. It should be appreciated that the projection 128 of the three-dimensional image and a projection 130 of the two-dimensional image can co-projected in the hologram 126. In particular, the augmented reality system 102 can be a mixed reality (MR) display such as a MR smart glasses or a MR head-mounted display. Nonlimiting examples of the augmented reality system 102 include the Magic Leap One® or the Microsoft HoloLens®. It should be appreciated that other types of MR displays may be used for the augmented reality system 102, as long as they are capable of superimposing computer-generated imagery over real-world objects. Additionally, although the augmented reality system 102 is described primarily herein as being a head-mounted display, it should be understood that other types of display that are not head-mounted, but which are capable of generating and superimposing the holograms over the real-world views may also be employed, as desired.

It should be appreciated that in instances where the augmented reality system 102 does not contain the computer system 106, the augmented reality system 102 can further include an additional non-transitory memory and a processing unit (that may include one or more hardware processors) that can aid in the rendering or generation of hologram 126. The augmented reality system 102 can also include a camera to record one or more images, one or more image-generation components to generate/display a visualization of the holograms, and/or other visualization and/or recording elements.

In yet further examples, it should be appreciated that the augmented reality system 102 can also include a plurality of positional sensors 132. The plurality of positional sensors 132 of the augmented reality system 102 are configured to determine various positional information for the augmented reality system 102, such as the approximated position in three-dimensional (3D) space, orientation, angular velocity, and acceleration of the augmented reality system 102. In particular, it should be understood that this allows the holographic imagery to be accurately displayed on the field of view of the practitioner, in operation.

Nonlimiting examples of the plurality of positional sensors 128 can include accelerometers, gyroscopes, electromagnetic sensors, and optical tracking sensors. It should further be appreciated that a skilled artisan may employ different types and numbers of the plurality of positional sensors 128 of the augmented reality system 102, for example, as required by the procedure or situation within which the augmented reality system 102 is being used.

Figure 3:
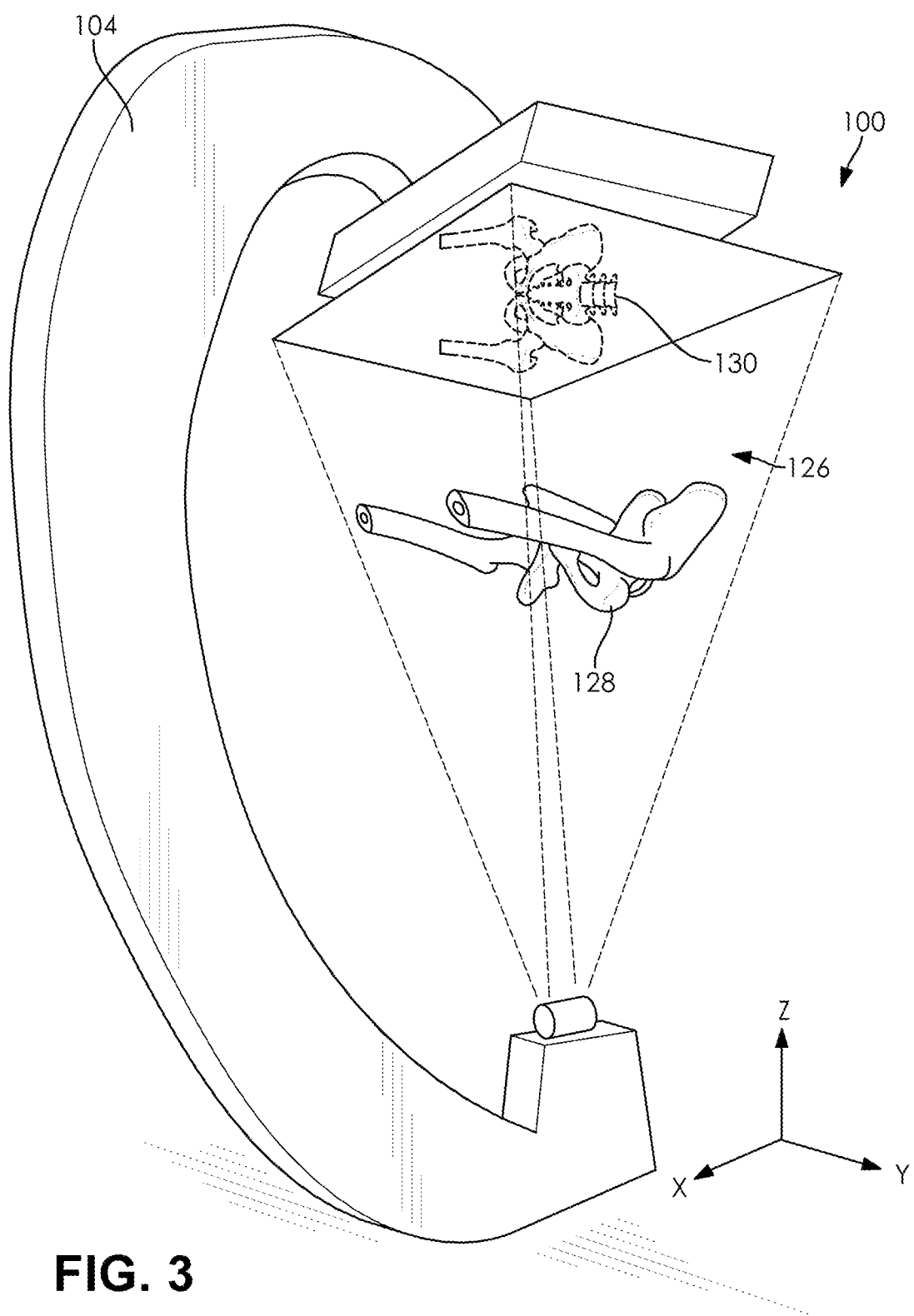
FIG. 3 is a top perspective view of a portion of the system of FIG. 1, further depicting a hologram as viewed through the augmented reality system.

As shown in FIG. 3, for example, the hologram 126 generated by the augmented reality system 102 can include the projection of the three-dimensional image 128 and the projection of the two-dimensional image 130. The projection of the three-dimensional image 128 generated by the augmented reality system 102 can be based on the image dataset from the patient. The projection of the two-dimensional image 130 generated by the augmented reality system 102 can be based on the two-dimensional image 116 from the patient. Since the projections can be stereoscopically linked by the computer system, the system 100 can allow the practitioner to visualize a point 134 on the projection 128 of the three-dimensional image and a corresponding point 136 on the projection of the two-dimensional image 130 during the procedure. In certain embodiments, the augmented reality system 102 can project a line segment 138 between the point 134 on the projection of the three-dimensional image 128 and the corresponding point 136 on the projection of the two-dimensional image 130.

The line segment 138 can be illustrated in several ways, such as between the centroid, center of mass, closest points, etc. Other statistical methods like principal component analyses (PCA) can supplement the designation of the six degrees of freedom the two data sets need to align to. Machine Learning can also be employed to recognize and automate alignment of like anatomical landmarks. Furthermore, statistical shape modeling from a database of like anatomy can inform the practitioner of population percentiles of anatomical and morphological features to inform trajectories and treatment titering. The automated or manual alignment can be illustrated with color or size gradients of the segments 138.

The augmented reality system 102 can further be configured to show a plurality of operating information or details to the practitioner in addition to rendering or generating the hologram 126. For example, the augmented reality system 102 can project the plurality of operating information over real-world objects, such as the patient. The operating information may include real-time navigation instructions or guidance for the trajectory to be employed, for example.

Desirably, this generating of the operating information or details allows the practitioner to simultaneously view the patient and the plurality of operating information in the same field of view. Also, the generating of the operating information or details together with the hologram 126 permits the practitioner to plan, size, or pre-orient any tracked instruments in operation. In certain embodiments, the augmented reality system 102 can track the C-arm system and likewise project a holographic representation of the C-arm components.

The system 100 of the present disclosure can be used to integrate tracked surgical instruments. The tracked instrument can be integrated and calibrated through the first image acquisition system 108. If a tracked surgical instrument is integrated and calibrated with the C-arm system 104, the movement of the tracked instrument can be shown in the hologram 126. It should be appreciated that the use and operability of an example tracked instrument is described in U.S. Pat. No. 10,895,906 to West et al., and also applicant's co-owned U.S. patent application Ser. No. 17/163,975 to Black et al., the entire disclosures of which are incorporated herein by reference.

As shown in FIG. 1, the computer system 106 can be in communication with the augmented reality system 102 and the C-arm system. The computer system 106 can be configured to store and generate the plurality of operating information, either thorough manual intervention by the practitioner or other medical professionals, or automatically based on the machine-readable instructions 122 encoded onto the memory 120. For example, the plurality of operating information may be generated in the augmented reality system 102 depending on a sensor-determined position or orientation of the tracked instrument 104 such as by algorithms, artificial intelligence (AI) protocols, or other practitioner-inputted data or thresholds.

In addition, the computer system 106 can be further configured to permit the practitioner to selectively adjust the plurality of operating information in real-time. For example, the practitioner can be able to adjust the position or orientation of the trajectory hologram 128. In addition, the practitioner can be able to decide which of the plurality of operating data is actively being shown to the practitioner. It should be appreciated that other settings and attributes of the plurality of operating information can be adjusted by practitioner in real-time, within the scope of this disclosure.

In particular, it should be understood that the augmented reality system 102 of the present disclosure advantageously permits the practitioner to perform a method 200 for performing the procedure on the patient while viewing the patient and the hologram 126 with the augmented reality system 102.

Figure 2:
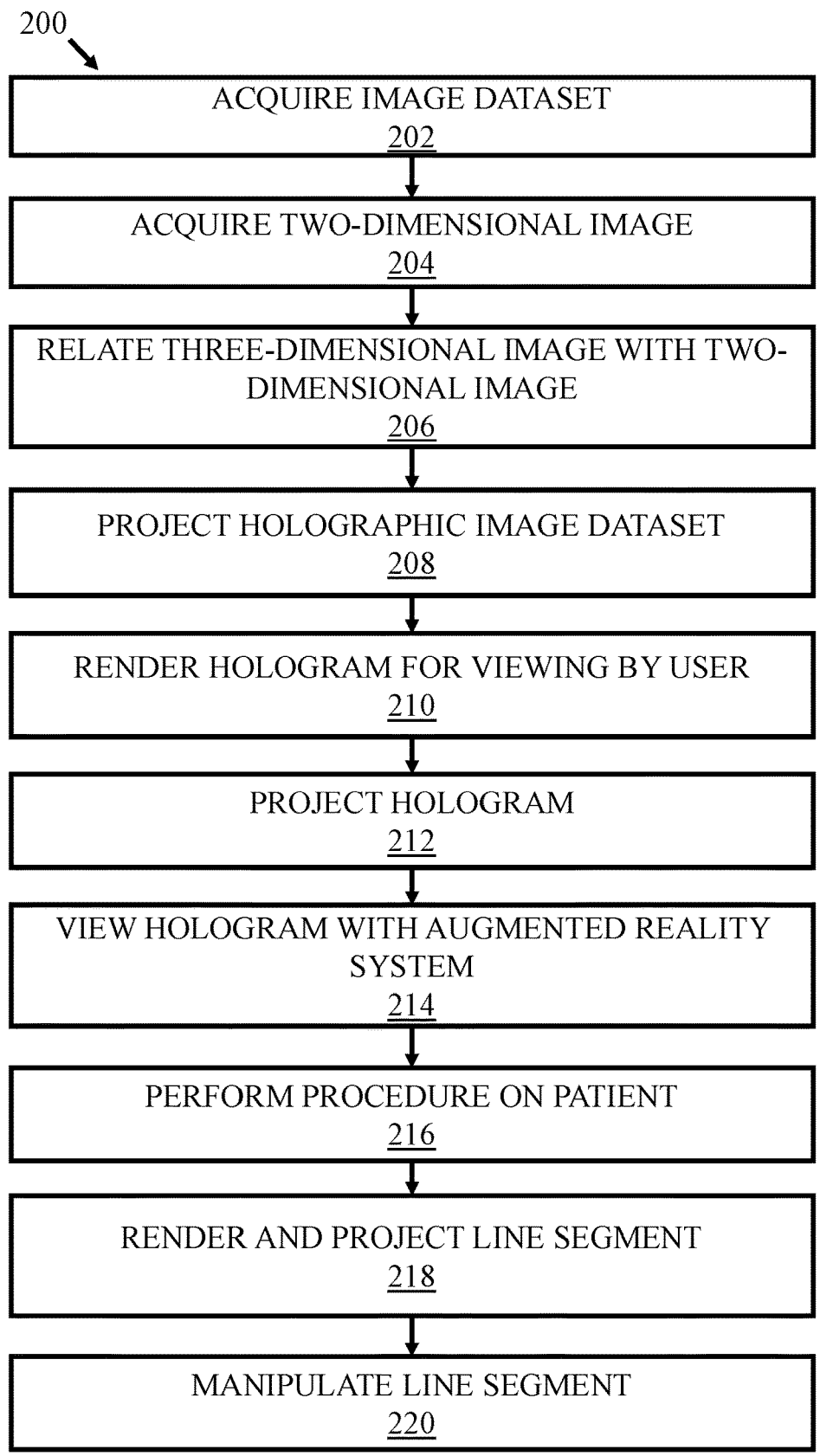
FIG. 2 is flowchart depicting a method for performing a procedure on a patient utilizing an augmented reality system.

With reference to FIG. 2, a method 200 for performing the procedure on the patient utilizing the augmented reality system 102, according to one embodiment of the present disclosure is shown. The method 200 can include a step 202 of acquiring, by the first image acquisition system 108, the image dataset including multiple images. The image dataset forming the three-dimensional image 114 of the location of interest on the patient. In particular, the image dataset can be acquired via cone-beam computed tomography imaging. The first image acquisition system 108 can move about the patient to provide the three-dimensional image 114.

The method 200 can include a step 204 of acquiring the two-dimensional image 116 of the location of interest on the patient. The two-dimensional image 116 can be acquired intraprocedurally and can be a fluoroscopic image. The two-dimensional image 116 can be acquired via the second image acquisition system 110. It should be appreciated that that acquiring the two-dimensional image 116 can be repeated, as necessary, throughout the procedure. Advantageously, this allows the practitioner to have a "live" image of the patient at all times throughout the procedure.

The method 200 can include a step 206 of relating, by the computer system 106, the three-dimensional image 114 with the two-dimensional image 116 to form the holographic image dataset. The computer system 106 can establish an input geometry between the patient, the three-dimensional image 114, and the two-dimensional image 116. The input geometry can be relative to the geometry of the C-arm system 104. In other embodiments, the input geometry can be relative to a multi-degree of freedom robotic arms.

The method 200 can include a step 208 of projection, by the augmented reality system 102, the holographic image dataset with the patient. The step 208 can include registration of the holographic image dataset. Registration of the holographic image dataset can be performed by the computer systems according to any suitable method including non-contact and non-optical methods. Additional methods for registration can include object recognition, photogammetry, and videogammetry via sensors or one or more cameras with IR, optical, and depth sensors, as non-limiting examples. Registration can also include corrections for gross patient motion relative to the C-arm system 104. For example, fiducial markers on the patient's skin can also be imaged with CBCT to correct for gross patient motion relative to the imaging frustum. The cameras can also adjust for respiration, heart rate, blood pressure, and heart rhythm with the non-contact sensors. For example, respiration can be tracked by artificial intelligence with contactless sensors.

Figure 4:
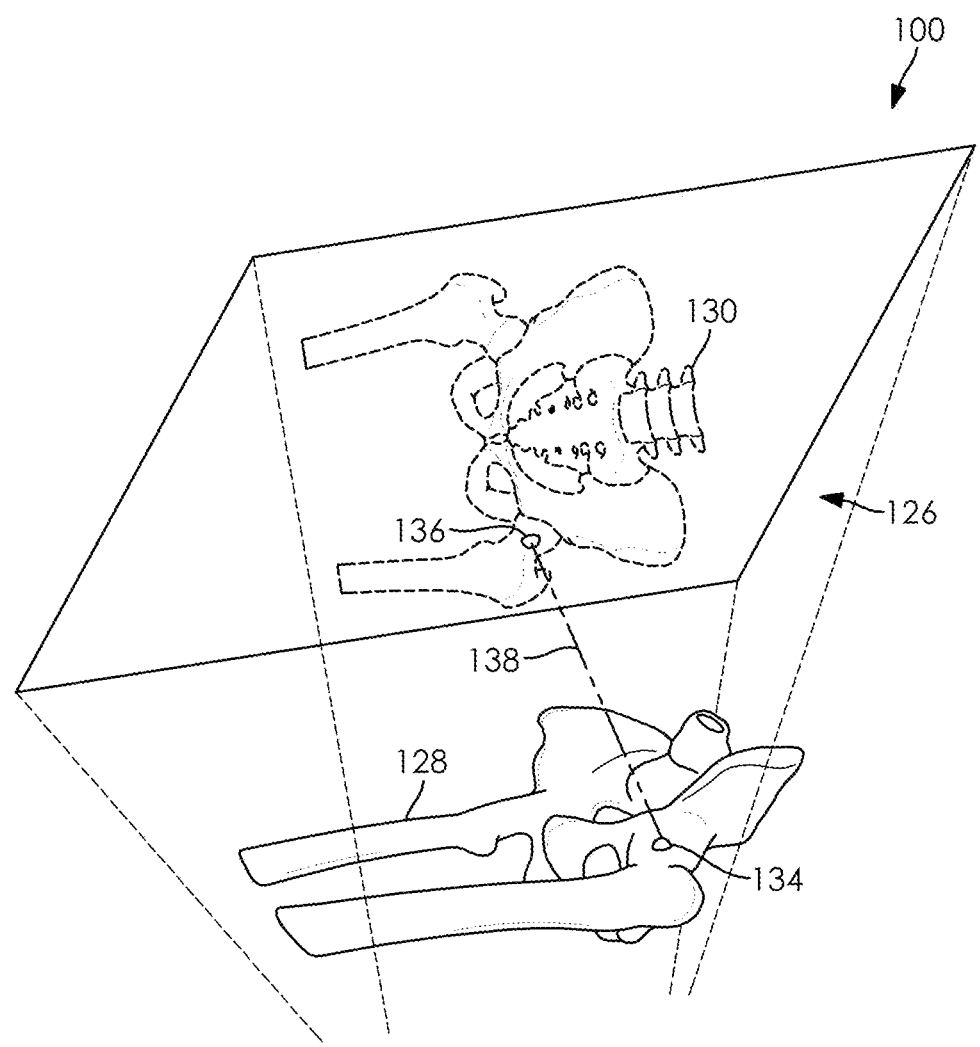
FIG. 4 is an enlarged top perspective view of the hologram as viewed through the augmented reality system of FIG. 3.

The method 200 can include a step 210 of rendering, by the augmented reality system 102, the hologram 126 based on the holographic image dataset from the patient for viewing by the practitioner. The method 200 can include a step 212 of projecting, by the augmented reality system 102, the hologram 126 within coordinates of the augmented reality system 102 based on a geometry of the C-arm system 104. As shown in FIGS. 3-4, the hologram 126 can include the projection 128 of the three-dimensional image 114 and the projection 130 of the two-dimensional image 116.

The method 200 can include a step 214 of viewing, by the practitioner, the hologram 126 with the augmented reality system 102 and a step 216 of performing, by the practitioner, the procedure on the patient. In certain embodiments, viewing, by the practitioner, the hologram 126 with the augmented reality system 102 and performing, by the practitioner, the procedure on the patient can be performed simultaneously. In other embodiments, these steps can be performed separately.

When the practitioner employs the augmented reality system 102, the practitioner can visualize the point 134 on the projection 128 of the three-dimensional image 114 and a corresponding point 136 on the projection 130 of the two-dimensional image 116 during the procedure. The method 200 can include a step 218 of rendering and projecting, by the augmented reality system 102, the line segment 138 between the point 134 on the projection 128 of the three-dimensional image 114 and a corresponding point 136 on the projection 130 of the two-dimensional image 116.

The method 200 can include a step 220 of manipulating, by the practitioner, an orientation of the hologram 126, and the line segment is likewise reoriented with respect to the hologram 128. To enhance visualization of the hologram 126 and eye-hand-coordination, the operator can interact with the hologram 126 (e.g., using far or near interaction of the Mixed Reality Toolkit) to adjust the pose of hologram 126 including the imaging frustum and modeled (virtual) components based on the C-arm geometry, such as rotation about the C-arm's systems isocenter, relative to and cross-reference with the CBCT's holographic representation of the patient anatomy in order the plan an updated pose of the physical C-arm 104 with less ionizing radiation burden and skin dose.

Figure 5:
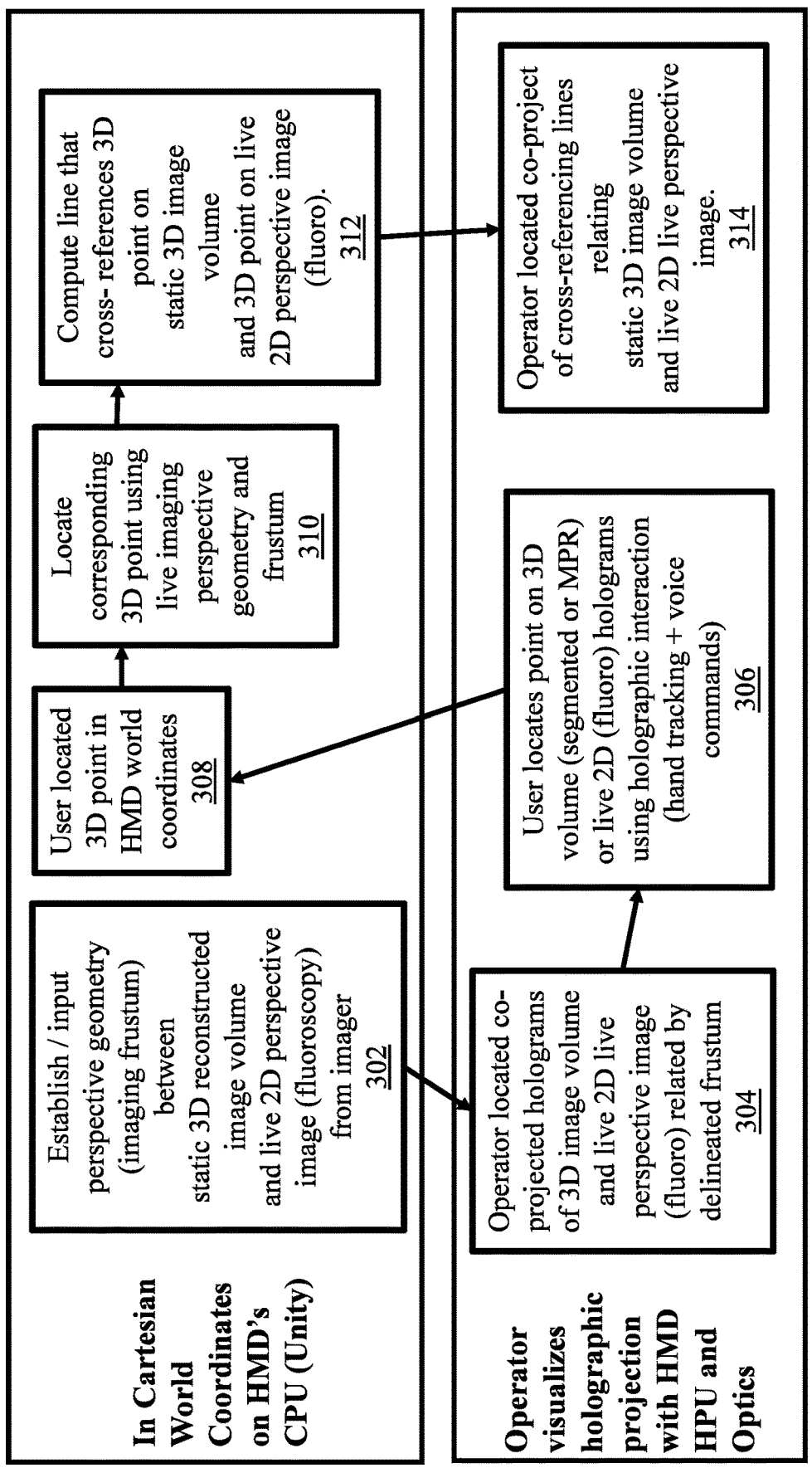
FIG. 5 is a flowchart depicting a method for performing a procedure on a patient utilizing an augmented reality system.

With reference to FIG. 5, a method 300 for performing the procedure on the patient utilizing the augmented reality system 102, according to one embodiment of the present disclosure is shown. The method 300 can include: a step 302 of establishing input perspective geometry (imaging frustum) between static 3D reconstructed image volume and live 2D perspective image (fluoroscopy) from imager; a step 304 of viewing, by the operator, located co-projected holograms of 3D image volume and live 2D live perspective image (fluoroscopy) related by delineated frustum; a step 306 of the operator locating a point on 3D image or live 2D (fluoro) holograms using holographic interaction (hand tracking and voice commands); a step 308 of the user locating the 3D point in HMD world coordinates; a step 310 of locating corresponding 3D point using live imaging perspective geometry and frustum; a step 312 of computing line that cross-references 3D point on static 3D image volume and 3D point on live 2D perspective image (fluoro); and a step 314 of the operator locating a co-project of cross-referencing lines relating static 3D image volume and live 2D live perspective image. It should be appreciated that a live ultrasound image can be provided in the cartesian coordinates, which can allow the practitioner to cross-reference with the two-dimensional live perspective image. In particular, the practitioner can further employ the augmented reality system 102 to visualize the live ultrasound, in registration with the three-dimensional holographic image and/or the tracked instrument if either or both of these are also employed, and cross-reference each of these with the real time fluoroscopy.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A method for performing a procedure on a patient utilizing an augmented reality system, the method comprising:
   acquiring, by a first image acquisition system, an image dataset including multiple images, the image dataset forming a three-dimensional image of a location of interest on the patient, wherein the first image acquisition system is one of a cone-beam computed tomography imaging system and a multidetector row computed tomography imaging system;
   acquiring a two-dimensional image of the location of interest on the patient;
   relating, by a computer system, the three-dimensional image with the two-dimensional image to form a three-dimensional holographic image dataset;
   projecting, by the augmented reality system, the holographic image dataset with the patient;
   rendering, by the augmented reality system, a hologram based on the holographic image dataset from the patient for three-dimensional stereoscopic viewing by a practitioner, the hologram including a projection of the three-dimensional image and a projection of the two-dimensional image;
   viewing, by the practitioner, the hologram with the augmented reality system; and
   performing, by the practitioner, the procedure on the patient;
   wherein the practitioner employs the augmented reality system to visualize and cross-reference a selected point on the projection of the three-dimensional image and a corresponding point on the projection of the two-dimensional image during the procedure.

2. The method of claim 1, wherein the first image acquisition system is moved about the patient to acquire the image dataset.

3. The method of claim 1, wherein the two-dimensional image is obtained intraprocedurally.

4. The method of claim 1, wherein the three-dimensional image includes multiplanar reformation of cone-beam computed tomography.

5. The method of claim 1, wherein the two-dimensional image is acquired via a second image acquisition system.

6. The method of claim 1, wherein the augmented reality system includes a headset display wearable by the practitioner for viewing the hologram.

7. The method of claim 6, wherein the computer system is integrated into the headset display wearable by the practitioner.

8. The method of claim 1, wherein the augmented reality system includes a tracked instrument, the tracked instrument having a plurality of sensors, and the computer system is in communication with the augmented reality system and the tracked instrument.

9. The method of claim 8, further comprising tracking, by the computer system, the tracked instrument using the plurality of sensors to provide a tracked instrument dataset.

10. The method of claim 1, wherein the two-dimensional image is real time fluoroscopy from the C-arm system.

11. The method of claim 10, wherein the practitioner further employs the augmented reality system to visualize live ultrasound, in registration with the hologram, and cross-reference with the real time fluoroscopy.

12. The method of claim 1, wherein viewing, by the practitioner, the hologram with the augmented reality system, and performing, by the practitioner, the procedure on the patient are performed simultaneously.

13. The method of claim 1, wherein the first image acquisition system includes a C-arm system.

14. The method of claim 13, further comprising projecting, by the augmented reality system, the hologram within coordinates of the augmented reality system based on a geometry of the C-arm system.

15. The method of claim 1, further comprising rendering, by the augmented reality system, a line segment between the point on the projection of the three-dimensional image and the corresponding point on the projection of the two-dimensional image.

16. The method of claim 14, further comprising manipulating, by the practitioner, an orientation of the hologram wherein the line segment is likewise reoriented to maintain registration with respect to the hologram.

17. The method of claim 1, further comprising manipulating, by the practitioner, of a position, an orientation, or a scale of the projection of the three-dimensional image and the projection of the two-dimensional image while maintaining perspective projection and cross-referencing relationship between the three-dimensional image and the projection of the two-dimensional image.

18. A system for performing a procedure on a patient by a practitioner, comprising:
   an augmented reality system configured to render a hologram;
   a first image acquisition system configured to acquire an image dataset from the patient, the image dataset forming a three-dimensional image of a location of interest on the patient, wherein the first image acquisition system is one of a cone-beam computed tomography imaging system and a multidetector row computed tomography imaging system; and a computer system with a processor and a memory, the computer system in communication with the augmented reality system and the first image acquisition system, and configured by machine-readable instructions to:

relate the three-dimensional image of the location of interest on the patient with a two-dimensional image of the location of interest on the patient to form a holographic image dataset; and register the holographic image dataset with the patient, wherein the augmented reality system is configured to:

render the hologram based on the holographic image dataset from the patient for three-dimensional stereoscopic viewing by a practitioner, the hologram including a projection of the three-dimensional image and a projection the two-dimensional image, and permit the practitioner to visualize a point on the projection of the three-dimensional image and a corresponding point on the projection of the two-dimensional image during the procedure.

19. The system of claim 18, wherein the first image acquisition system includes a C-arm system.

\* \* \* \* \*